(12) United States Patent
Eidenschink

(10) Patent No.: US 9,642,706 B2
(45) Date of Patent: May 9, 2017

(54) APPARATUS AND METHOD FOR HEART VALVE REPAIR

(71) Applicant: St. Jude Medical, Inc., St. Paul, MN (US)

(72) Inventor: Tracee Eidenschink, Wayzata, MN (US)

(73) Assignee: St. Jude Medical, LLC, Abbott Park, IL (US)

( * ) Notice: Subject to any disclaimer, the term of this patent is extended or adjusted under 35 U.S.C. 154(b) by 408 days.

(21) Appl. No.: 14/195,355

(22) Filed: Mar. 3, 2014

(65) Prior Publication Data

US 2014/0257347 A1    Sep. 11, 2014

Related U.S. Application Data

(60) Provisional application No. 61/776,470, filed on Mar. 11, 2013.

(51) Int. Cl.
| | | |
|---|---|---|
| *A61F 2/24* | (2006.01) | |
| *A61B 17/128* | (2006.01) | |
| *A61B 17/122* | (2006.01) | |

(52) U.S. Cl.
CPC ............ *A61F 2/2466* (2013.01); *A61F 2/246* (2013.01); *A61B 17/122* (2013.01); *A61B 17/128* (2013.01)

(58) Field of Classification Search
CPC ...... A61F 2/246; A61F 2/2466; A61B 17/122; A61B 17/128; A61B 17/00234
See application file for complete search history.

(56) References Cited

U.S. PATENT DOCUMENTS

| | | | |
|---|---|---|---|
| 5,156,608 A | | 10/1992 | Troidl et al. |
| 5,499,991 A | * | 3/1996 | Garman ............ A61B 17/0483 606/148 |

(Continued)

FOREIGN PATENT DOCUMENTS

| | | |
|---|---|---|
| AU | 2002300522 B2 | 1/2007 |
| WO | 9620749 A1 | 7/1996 |

(Continued)

OTHER PUBLICATIONS

Merriam-Webster definition of "fabric" as accessed on Dec. 17, 2014; http://www.merriam-webster.com/dictionary/fabric.

(Continued)

*Primary Examiner* — Jing Ou
(74) *Attorney, Agent, or Firm* — Lerner, David, Littenberg, Krumholz & Mentlik, LLP

(57) ABSTRACT

A device for transcatheter gathering of tissue of a heart valve leaflet may include an elongated tube extending in a longitudinal direction and having an open distal end, a tissue securing component disposed at the distal end of the elongated tube, and a capture tool movable in the elongated tube between a retracted position and an extended position. The elongated tube may have an inner surface and a lumen extending therethrough. The tissue securing component may include a clip having a roller and a support element. The roller may be rotatable relative to the support element. The capture tool may be operable to capture tissue of the heart valve leaflet and to draw the captured tissue into the tissue securing component. The tissue securing component may be adapted to be applied to the captured tissue to hold the captured tissue in a gathered configuration.

20 Claims, 5 Drawing Sheets

(56) References Cited

U.S. PATENT DOCUMENTS

| | | | |
|---|---|---|---|
| 5,601,573 A | 2/1997 | Fogelberg et al. | |
| 5,741,278 A * | 4/1998 | Stevens | A61B 17/12013 |
| | | | 606/139 |
| 5,749,879 A | 5/1998 | Middleman et al. | |
| 5,921,993 A | 7/1999 | Yoon | |
| 6,258,105 B1 | 7/2001 | Hart et al. | |
| 6,440,152 B1 | 8/2002 | Gainor et al. | |
| 6,569,182 B1 | 5/2003 | Balceta et al. | |
| 6,626,930 B1 | 9/2003 | Allen et al. | |
| 6,752,813 B2 | 6/2004 | Goldfarb et al. | |
| 6,945,978 B1 | 9/2005 | Hyde | |
| 7,011,669 B2 | 3/2006 | Kimblad | |
| 7,464,712 B2 | 12/2008 | Oz et al. | |
| 7,569,062 B1 | 8/2009 | Kuehn et al. | |
| 7,758,595 B2 | 7/2010 | Allen et al. | |
| 8,777,966 B2 | 7/2014 | Dale et al. | |
| 8,951,285 B2 | 2/2015 | Sugimoto et al. | |
| 2001/0016750 A1 | 8/2001 | Malecki et al. | |
| 2002/0010388 A1 * | 1/2002 | Taylor | A61B 17/00234 |
| | | | 600/204 |
| 2002/0013571 A1 | 1/2002 | Goldfarb et al. | |
| 2002/0035390 A1 * | 3/2002 | Schaldach | A61F 2/958 |
| | | | 623/1.11 |
| 2002/0049457 A1 * | 4/2002 | Kaplan | A61B 17/12 |
| | | | 606/139 |
| 2002/0107531 A1 | 8/2002 | Schreck et al. | |
| 2002/0183768 A1 * | 12/2002 | Deem | A61B 17/064 |
| | | | 606/151 |
| 2003/0065335 A1 * | 4/2003 | Guido | A61B 17/12013 |
| | | | 606/144 |
| 2003/0093071 A1 | 5/2003 | Hauck et al. | |
| 2003/0120264 A1 | 6/2003 | Lattouf | |
| 2004/0030335 A1 * | 2/2004 | Zenati | A61B 17/12013 |
| | | | 606/51 |
| 2004/0039442 A1 | 2/2004 | St. Goar et al. | |
| 2004/0087985 A1 | 5/2004 | Loshakove et al. | |
| 2004/0176784 A1 * | 9/2004 | Okada | A61B 17/1285 |
| | | | 606/142 |
| 2004/0181238 A1 | 9/2004 | Zarbatany et al. | |
| 2004/0193185 A1 | 9/2004 | McBrayer | |
| 2005/0004583 A1 | 1/2005 | Oz et al. | |
| 2005/0090837 A1 | 4/2005 | Sixto et al. | |
| 2005/0096671 A1 | 5/2005 | Wellman et al. | |
| 2005/0107871 A1 | 5/2005 | Realyvasquez et al. | |
| 2005/0125011 A1 | 6/2005 | Spence et al. | |
| 2005/0143763 A1 | 6/2005 | Ortiz et al. | |
| 2005/0149072 A1 | 7/2005 | DeVries et al. | |
| 2005/0177176 A1 | 8/2005 | Gerbi et al. | |
| 2005/0251161 A1 | 11/2005 | Saadat et al. | |
| 2006/0089671 A1 | 4/2006 | Goldfarb et al. | |
| 2006/0122633 A1 | 6/2006 | To et al. | |
| 2006/0173422 A1 | 8/2006 | Reydel et al. | |
| 2006/0173473 A1 * | 8/2006 | Bob | A61B 1/00151 |
| | | | 606/153 |
| 2007/0049952 A1 | 3/2007 | Weiss | |
| 2007/0093857 A1 | 4/2007 | Rogers et al. | |
| 2007/0102474 A1 | 5/2007 | Shelton et al. | |
| 2007/0102475 A1 | 5/2007 | Ortiz et al. | |
| 2007/0142846 A1 | 6/2007 | Catanese et al. | |
| 2007/0162056 A1 | 7/2007 | Gerbi et al. | |
| 2007/0197858 A1 | 8/2007 | Goldfarb et al. | |
| 2007/0198032 A1 | 8/2007 | Ortiz | |
| 2007/0225734 A1 | 9/2007 | Bell et al. | |
| 2008/0125796 A1 | 5/2008 | Graham | |
| 2008/0234705 A1 | 9/2008 | Cropper et al. | |
| 2008/0255427 A1 | 10/2008 | Satake et al. | |
| 2008/0294175 A1 | 11/2008 | Bardsley et al. | |
| 2008/0300624 A1 | 12/2008 | Schwemberger et al. | |
| 2008/0319455 A1 | 12/2008 | Harris et al. | |
| 2009/0062852 A1 | 3/2009 | Marino | |
| 2009/0118744 A1 | 5/2009 | Wells et al. | |
| 2009/0125038 A1 | 5/2009 | Ewers et al. | |
| 2009/0149870 A1 | 6/2009 | Jugenheimer et al. | |
| 2011/0054521 A1 | 3/2011 | Ventura et al. | |
| 2011/0077668 A1 | 3/2011 | Gordon et al. | |
| 2011/0087242 A1 | 4/2011 | Pribanic et al. | |
| 2011/0114700 A1 | 5/2011 | Baxter, III et al. | |
| 2011/0230897 A1 | 9/2011 | Palermo et al. | |
| 2011/0313432 A1 | 12/2011 | Miles et al. | |
| 2012/0022532 A1 * | 1/2012 | Garrison | A61B 18/14 |
| | | | 606/52 |
| 2012/0109159 A1 * | 5/2012 | Jordan | A61B 17/1285 |
| | | | 606/142 |
| 2012/0226291 A1 | 9/2012 | Malizia et al. | |
| 2013/0046332 A1 | 2/2013 | Jones et al. | |
| 2014/0039607 A1 | 2/2014 | Kovach | |

FOREIGN PATENT DOCUMENTS

| | | |
|---|---|---|
| WO | 9900059 A1 | 1/1999 |
| WO | 0128432 A1 | 4/2001 |
| WO | 0139672 A2 | 6/2001 |
| WO | 0182847 A2 | 11/2001 |
| WO | 0200121 A1 | 1/2002 |
| WO | 03049619 A2 | 6/2003 |
| WO | 2006039199 A2 | 4/2006 |
| WO | 2007027451 A2 | 3/2007 |
| WO | 2008068756 A2 | 6/2008 |
| WO | 2008121738 A2 | 10/2008 |
| WO | 2009087592 A2 | 7/2009 |
| WO | 2010094896 A1 | 8/2010 |
| WO | 2011053673 A1 | 5/2011 |
| WO | 2012087724 A1 | 6/2012 |
| WO | 2012106398 A1 | 8/2012 |
| WO | 2013019415 A1 | 2/2013 |
| WO | 2013116617 A1 | 8/2013 |
| WO | 2014022464 A1 | 2/2014 |

OTHER PUBLICATIONS

International Search Report for Application No. PCT/US2012/023437 dated Apr. 24, 2012.

International Search Report and Written Opinion for Application No. PCT/US2013/052843 dated Oct. 11, 2013.

International Search Report and Written Opinion for Application No. PCT/US2013/052838 dated Oct. 11, 2013.

International Search Report and Written Opinion for Application No. PCT/US2013/052822 dated Jan. 21, 2014.

International Preliminary Report on Patentability for Application No. PCT/U52012/023437 dated Aug. 6, 2013.

International Search Report for Application No. PCT/US2013/023077 dated May 14, 2013.

International Search Report and Written Opinion for Application No. PCT/US2013/023082 dated Oct. 1, 2013.

International Search Report and Written Opinion for Application No. PCT/US2013/024304 dated Jul. 5, 2013.

International Search Report for Application No. PCT/US2013/052832 dated Jan. 15, 2014.

International Search Report and Written Opinion for Application No. PCT/US2013/065360 dated Apr. 23, 2014.

* cited by examiner

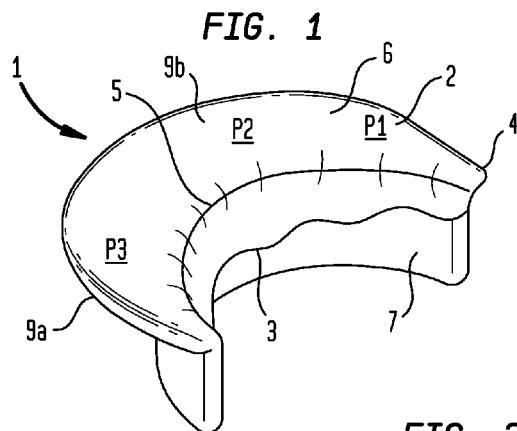
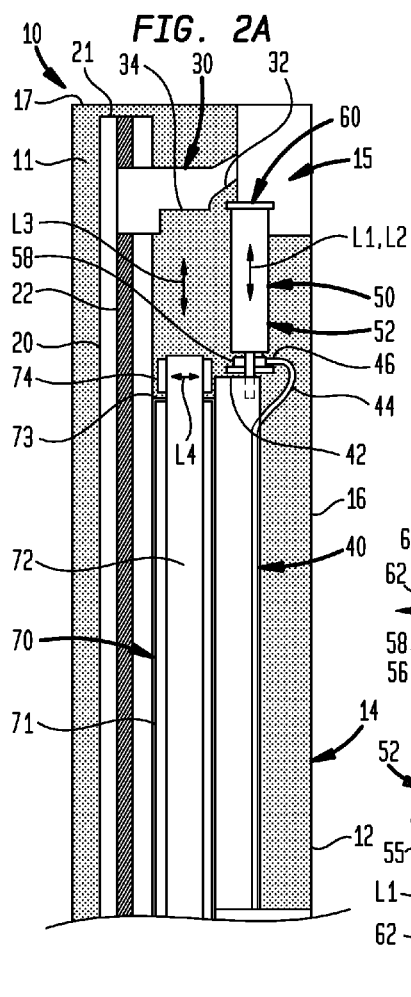
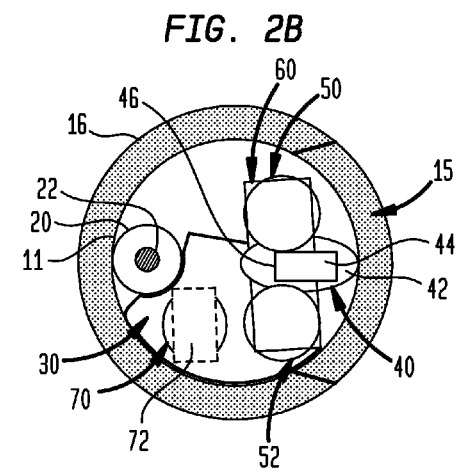
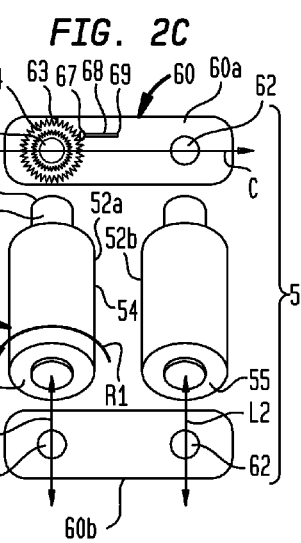
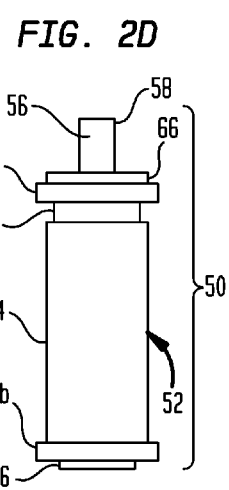
FIG. 1
FIG. 2A
FIG. 2B
FIG. 2C
FIG. 2D

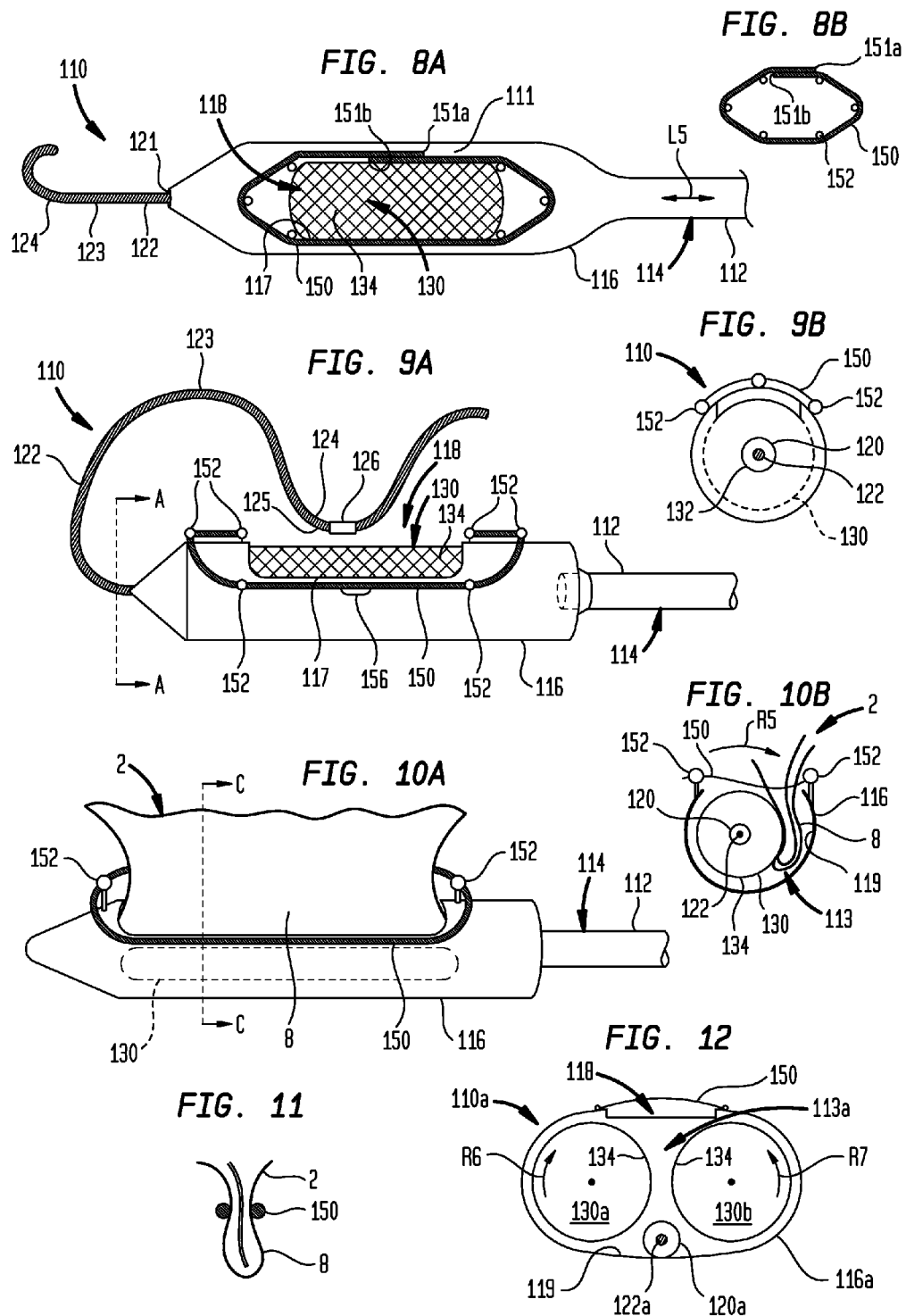

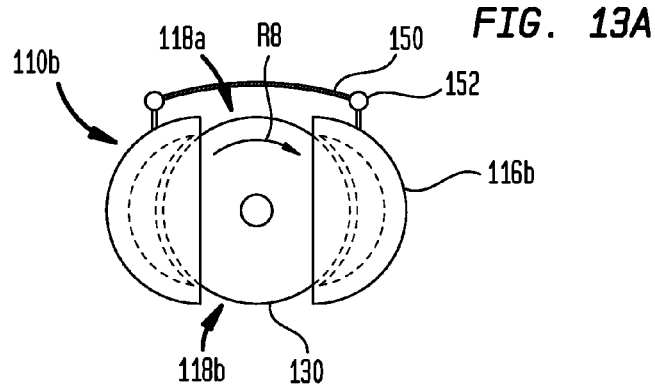
FIG. 13A
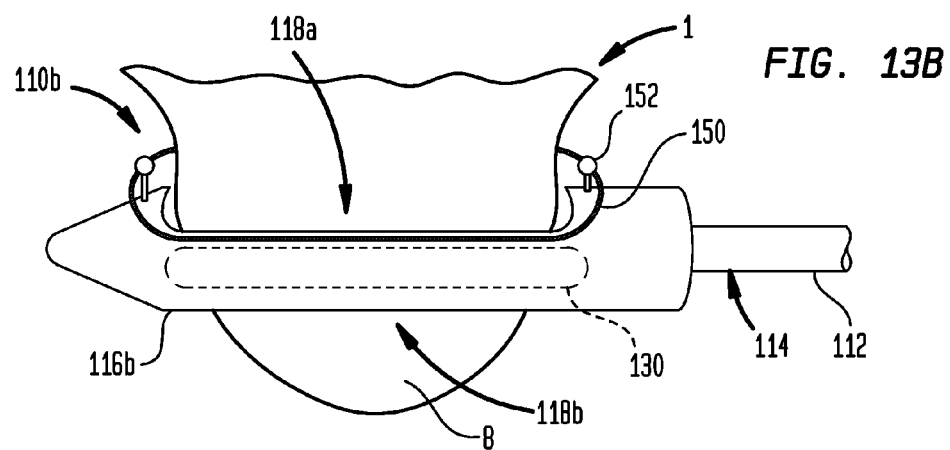
FIG. 13B
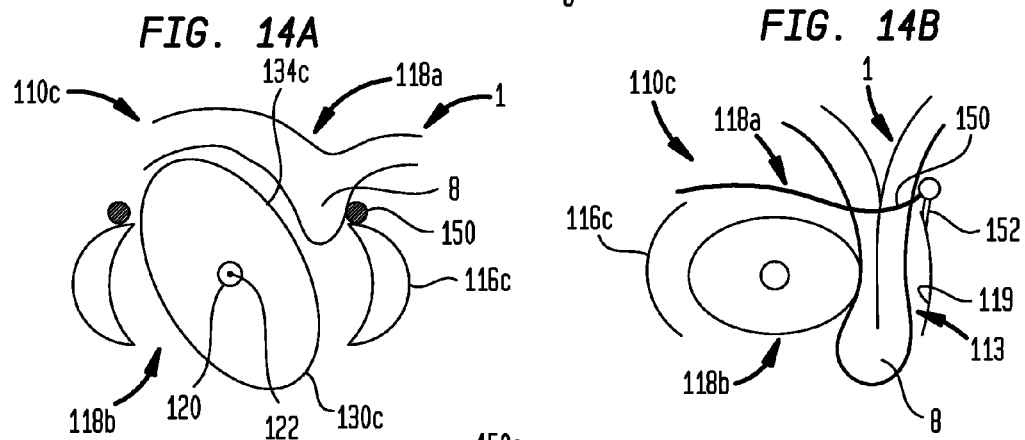
FIG. 14A
FIG. 14B
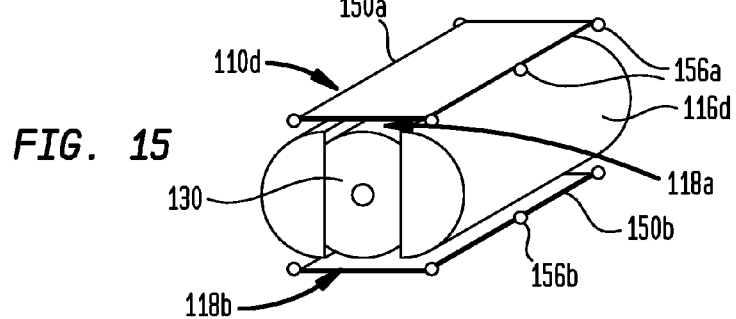
FIG. 15

APPARATUS AND METHOD FOR HEART VALVE REPAIR

CROSS-REFERENCE TO RELATED APPLICATION

The present application claims the benefit of the filing date of U.S. Provisional Patent Application No. 61/776,470 filed Mar. 11, 2013, the disclosure of which is hereby incorporated herein by reference.

BACKGROUND OF THE INVENTION

The present invention is related to heart valve repair, and more particularly to devices, systems, and methods for transcatheter repair of a heart valve leaflet.

Properly functioning heart valves can maintain unidirectional blood flow in the circulatory system by opening and closing, depending on the difference in pressure on each side of the valve. The two atrioventricular valves (mitral and tricuspid valves) are multicusped valves that prevent backflow from the ventricles into the atria during systole. They are anchored to the wall of the ventricle by chordae tendineae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which the abnormal mitral valve leaflets prolapse (i.e., a portion of the affected leaflet may be billowed, loose, and floppy). Furthermore, the chordae tendineae may stretch and thus become too long, or the chordae tendineae may be broken. As a result, the valve does not close normally, and the unsupported valve leaflet may bulge back, or "prolapse," into the left atrium like a parachute. Thus, as the ventricle contracts, the abnormal leaflet may be propelled backwards, beyond its normal closure line into the left atrium, thereby allowing blood to flow back into the left atrium and the lungs.

Mitral valve prolapse causes mitral regurgitation. Isolated posterior leaflet prolapse of the human heart mitral valve, i.e. prolapse of a single leaflet, is the most common cause of mitral regurgitation. The exact cause of the prolapse is not clear. Untreated mitral regurgitation may lead to congestive heart failure and pulmonary hypertension.

Despite the various improvements that have been made to devices and methods for mitral valve leaflet repair, there remain some shortcomings. For example, conventional methods of treating mitral valve prolapse include replacement of the mitral valve, clipping the two mitral valve leaflets to one another, and resection of the prolapsed segment using open heart surgery. Such surgical methods may be invasive to the patient and may require an extended recovery period.

There therefore is a need for further improvements to the current techniques for treating heart valve leaflet prolapse. Among other advantages, the present invention may address one or more of these needs.

BRIEF SUMMARY OF THE INVENTION

Devices and methods for gathering of heart valve leaflet tissue are disclosed. A device for transcatheter gathering of tissue of a heart valve leaflet may include an elongated tube extending in a longitudinal direction and having an open distal end, a tissue securing component disposed at the distal end of the elongated tube, and a capture tool movable in the elongated tube between a retracted position and an extended position. The elongated tube may have an inner surface and a lumen extending therethrough. The tissue securing component may include a clip having a roller and a support element. The roller may be rotatable relative to the support element. The capture tool may be operable to capture tissue of the heart valve leaflet and to draw the captured tissue into the tissue securing component. The tissue securing component may be adapted to be applied to the captured tissue to hold the captured tissue in a gathered configuration.

The roller may be a first roller and the support element may be a second roller. The second roller may be rotatable relative to the first roller. The second roller may be fixed relative to a rotational axis of the first roller. The support element may be fixed relative to a rotational axis of the roller. The tissue securing component may include a mechanism permitting rotation of the roller about a rotational axis of the roller only in a first rotational direction. The mechanism may prevent rotation of the roller in a second rotational direction opposite the first rotational direction. The tissue securing component may include two coupling plates extending between the roller and the support element. The roller may have an outer surface that is roughened, knurled, or having features that protrude from the outer surface.

The device may also include a drive assembly adapted to rotate the roller relative to the support element. The drive assembly may be movable in the elongated tube in the longitudinal direction. The drive assembly may be movable between a proximal position in which a distal end of the drive assembly is spaced apart from the roller and a distal position in which the distal end of the drive assembly contacts a portion of the roller. The drive assembly may include a belt extending around two rollers. The device may also include an actuation shaft movable in the elongated tube in the longitudinal direction. The actuation shaft may be adapted to move the tissue securing component therewith relative to the elongated tube.

The device may also include a contact plate having a guide surface disposed at an oblique angle relative to the longitudinal direction. The guide surface may be adapted to guide motion of the tissue securing component such that the roller pivots relative to the actuation shaft about an axis perpendicular to a rotational axis of the roller when the actuation shaft is moved distally. The device may also include a release wire removably coupled to the tissue securing component and extending through the elongated tube to a proximal end of the device. A distal end of the capture tool may have a hook shape. The capture tool may include a grasping wire slidably disposed in a containment tube. A distal portion of the grasping wire may be adapted to change from a linear shape to the hook shape when the distal portion of the grasping wire is extended out from the containment tube. The grasping wire may be partially or entirely made from a shape-memory material.

A transcatheter method of gathering tissue of a heart valve leaflet may include inserting a catheter assembly to a position adjacent the heart valve leaflet. The catheter assembly may include an elongated tube extending in a longitudinal direction and having an open distal end, a capture tool moveable between a retracted position and an extended position, and a tissue securing component including a roller and a support element. The method may also include moving the capture tool from the retracted position toward the extended position and manipulating the capture tool so that tissue of the heart valve leaflet is captured by the capture tool. The method may also include drawing the captured tissue between the roller and the support element by moving the capture tool to the extended position and rotating the roller in a first rotational direction to push the captured tissue through a gap located between the roller and the support element. The method may also include securing the captured tissue by preventing rotation of the roller in a second rotational direction opposite the first rotational direction to hold the captured tissue substantially in a gathered configuration.

The method may also include, after the securing step, detaching a release wire from the tissue securing component. The release wire may extend through the elongated tube to a proximal end of the device. The method may also include, before the rotating step, advancing the roller distally relative to the elongated tube in the longitudinal direction. The method may also include, before the rotating step, pivoting the roller relative to the elongated tube from a first orientation in which a rotational axis of the roller is oriented substantially parallel to the longitudinal direction to a second orientation in which the rotational axis of the roller is oriented substantially perpendicular to the longitudinal direction. The pivoting step may be performed by advancing the roller distally relative to the elongated tube in the longitudinal direction until the roller contacts a guide surface disposed at an oblique angle relative to the longitudinal direction. The contact with the guide surface may cause the roller to pivot relative to the elongated tube about an axis perpendicular to the rotational axis of the roller.

During the securing step, the rotation of the roller in the second rotational direction may be prevented by interaction of a spring lock member and teeth of a ratcheting cam affixed to the first roller and adapted to rotate therewith relative to the spring lock member. The rotating step may be performed by actuating a drive assembly in contact with the tissue securing component. The method may also include, before the rotating step, moving the drive assembly from an initial position in which a distal end of the drive assembly is spaced apart from the roller and an engaged position in which the distal end of the drive assembly contacts a portion of the roller.

The roller is a first roller and the support element may be a second roller. The second roller may be rotatable relative to the first roller. The rotating step may include rotating the second roller in the second rotational direction. During the rotating step, the rotation of the second roller may be caused by friction between the captured tissue and the first and second rollers, such that the rotation of the first roller in the first rotational direction forces the second roller to rotate in the second rotational direction. The capture tool may include a grasping wire slidably disposed in a containment tube. The moving step may be performed by sliding a distal end of the grasping wire out of the containment tube so that the distal portion of the grasping wire changes from a linear shape to a hook shape.

Another device for transcatheter gathering of tissue of a heart valve leaflet may include an elongated tube extending in a longitudinal direction and having an opening extending generally in the longitudinal direction and partially around a circumference of the elongated tube, a capture tool movable in the elongated tube between a retracted position and an extended position, a roller extending within the elongated tube and being rotatable relative to the elongated tube, and a tissue securing component disposed around a peripheral edge of the opening. The elongated tube may have a lumen therein defining an inner surface. The capture tool may be operable to capture tissue of the heart valve leaflet and to draw the captured tissue into the opening. The roller may be located adjacent the opening and may have a rotational axis substantially parallel to the longitudinal direction. The roller may define an outer surface spaced apart from the inner surface of the elongated tube. The roller may be operable to gather the captured tissue into a pocket within the elongated tube formed adjacent the outer surface of the roller. The tissue securing component may be adapted to be applied to the captured tissue to hold the captured tissue in a gathered configuration.

The opening may be a first opening. The elongated tube may have a second opening extending generally in the longitudinal direction and partially around the circumference of the elongated tube. The second opening may be located opposite the first opening in a direction perpendicular to the longitudinal direction. The roller may be operable to gather the captured tissue into the pocket and through the second opening. The tissue securing component may be a first tissue securing component. The device may also include a second tissue securing component disposed around a peripheral edge of the second opening and adapted to be applied to the captured tissue to hold the captured tissue in the gathered configuration. The outer surface of the roller may be roughened, knurled, or having features that protrude from the outer surface.

The roller may have a circular cross-sectional shape in a direction perpendicular to the rotational axis of the roller. The roller may have an oblong cross-sectional shape in a direction perpendicular to the rotational axis of the roller. The pocket may extend between the outer surface of the roller and the inner surface of the elongated tube. The tissue securing component may be a releasable clip configured to be held in an expanded condition around the peripheral edge of the opening until the clip is released. The clip may have one or more radiopaque markers thereon. The device may also include retention posts disposed around the peripheral edge of the opening. The retention posts may extend from an outer surface of the elongated tube in a direction substantially perpendicular to the outer surface. The clip may extend around the retention posts in the expanded condition and may be biased from the expanded condition to a clamping condition.

The retention posts may be retractable into the outer tube. The clip may be released from the retention posts when the retention posts are retracted into the outer tube. A distal end of the capture tool may have a hook shape. The capture tool may include a grasping wire slidably disposed in a lumen extending through the roller in the longitudinal direction. A distal portion of the grasping wire may be adapted to change from a linear shape to the hook shape when the distal portion of the grasping wire is extended out from the lumen. The grasping wire may be partially or entirely made from a shape-memory material. The grasping wire may have one or more radiopaque markers thereon. The roller may be a first roller. The device may also include a second roller extending within the elongated tube adjacent the first roller and being rotatable relative to the first roller. The second roller may have a rotational axis substantially parallel to the longitudinal direction. The pocket may extend between the first and second rollers.

Another transcatheter method of gathering tissue of a heart valve leaflet may include inserting a catheter assembly to a position adjacent the heart valve leaflet. The catheter assembly may include an elongated tube extending in a longitudinal direction, a capture tool moveable between a retracted position and an extended position, a roller extending within the elongated tube and located adjacent an opening of the elongated tube, and a tissue securing component disposed around a peripheral edge of the opening. The method may also include moving the capture tool from the retracted position toward the extended position and manipulating the capture tool so that tissue of the heart valve leaflet is captured by the capture tool. The method may also include drawing the captured tissue into the opening by moving the capture tool to the extended position and rotating the roller in a first rotational direction to push the captured tissue into a pocket within the elongated tube formed adjacent the outer surface of the roller. The method may also include securing the captured tissue by releasing the tissue securing component from the catheter assembly to the captured tissue so as to hold the captured tissue substantially in a gathered configuration.

The tissue securing component may be a releasable clip. During the inserting step, the clip may be held in an expanded condition around retention posts located around the peripheral edge of the opening. The securing step may be performed by retracting the retention posts into the outer tube. The clip may be released from the retention posts onto the captured tissue. The opening may be a first opening. The elongated tube may have a second opening located opposite the first opening in a direction perpendicular to the longitudinal direction. The rotating step may push the captured tissue into the pocket and through the second opening. The capture tool may include a grasping wire slidably disposed in a containment tube. The moving step may be performed by sliding a distal end of the grasping wire out of the containment tube so that the distal portion of the grasping wire changes from a linear shape to a hook shape.

The method may also include, after the securing step, releasing the captured tissue by rotating the roller in a second rotational direction opposite the first rotational direction to push the captured tissue out of the opening. The roller may be a first roller and the support element may be a second roller. The second roller may be rotatable relative to the first roller. The rotating step may include rotating the second roller in a second rotational direction opposite the first rotational direction. The pocket may be a gap extending between the first and second rollers. During the rotating step, the rotation of the second roller may be caused by friction between the captured tissue and the first and second rollers. Rotation of the first roller in the first rotational direction may force the second roller to rotate in the second rotational direction.

Yet another device for transcatheter gathering of tissue of a heart valve leaflet may include an elongated tube extending in a longitudinal direction and having an opening therein, a tissue gathering component disposed within the elongated tube adjacent the opening, and a capture tool movable in the elongated tube between a retracted position and an extended position. The tissue gathering component may include a roller and a support element. The capture tool may be operable to capture tissue of the heart valve leaflet and to draw the captured tissue into the tissue gathering component. The tissue gathering component may be adapted to gather the captured tissue between the roller and the support element when in an operating position.

The roller may be a first roller. The support element may comprise a second roller. The tissue gathering component may be adapted to be secured to the captured tissue to hold the captured tissue in a gathered configuration. The support element may comprise an inner surface of the elongated tube. The device may also include a tissue securing component disposed around a peripheral edge of the opening and adapted to be applied to the captured tissue to hold the captured tissue in a gathered configuration.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

FIG. 1 is a diagrammatic perspective view of the posterior leaflet of a mitral valve;

FIG. 2A is a diagrammatic longitudinal cross-sectional view of the distal portion of one embodiment of a device for transcatheter gathering of heart valve leaflet tissue, shown with the clip in an initial position;

FIG. 2B is a top plan view of the distal portion of the device of FIG. 2A;

FIG. 2C is an exploded perspective view of the clip of FIG. 2A;

FIG. 2D is a side view of the clip of FIG. 2A;

FIG. 8A is a diagrammatic top view of the distal portion of another embodiment of a device for transcatheter gathering of heart valve leaflet tissue;

FIG. 8B is a diagrammatic view of the clip and retention pegs of FIG. 8A;

FIG. 9A is a side view of the distal portion of the device of FIG. 8A, shown with the hook deployed;

FIG. 9B is an end view of the distal portion of the device of FIG. 8A;

FIG. 10A is a side view of the distal portion of the device of FIG. 8A, engaged with the posterior leaflet of the mitral valve of FIG. 1;

FIG. 10B is a cross-sectional view of the device of FIG. 10A, taken along the line C-C of FIG. 10A;

FIG. 11 is a cross-sectional view of the clip of FIG. 8A, engaged with the posterior leaflet of the mitral valve of FIG. 1;

FIG. 12 is a cross-sectional view of a distal portion of a variant of the device of FIG. 8A according to an alternate embodiment;

FIG. 13A is a cross-sectional view of a distal portion of a variant of the device of FIG. 8A according to another alternate embodiment;

FIG. 13B is a side view of the distal portion of the device of FIG. 13A, engaged with the posterior leaflet of the mitral valve of FIG. 1;

FIG. 14A is a cross-sectional view of a distal portion of another variant of the device of FIG. 8A according to yet another alternate embodiment;

FIG. 14B is a cross-sectional view of the device of FIG. 14A, shown with a captured portion of posterior leaflet tissue extending therethrough; and FIG. 15 is a perspective view of a distal portion of still another variant of the device of FIG. 8A according to another alternate embodiment.

DETAILED DESCRIPTION

Figures 3, 4A, 4B:
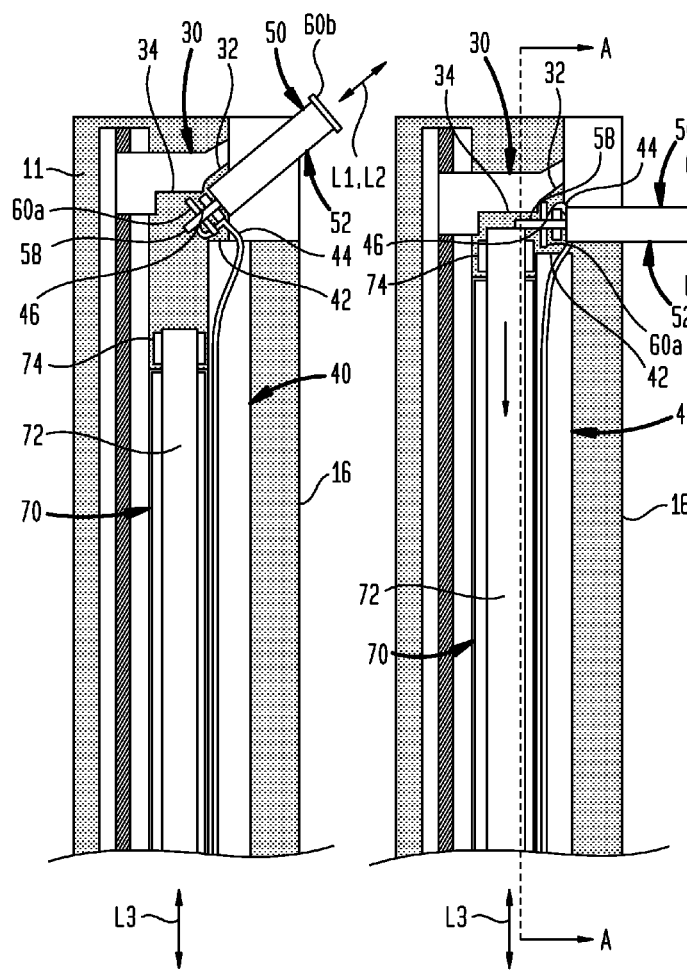
FIG. 3 is a longitudinal cross-sectional view of the distal portion of the device of FIG. 2A, shown with the clip in an intermediate position.
FIG. 4A is a longitudinal cross-sectional view of the distal portion of the device of FIG. 2A, shown with the clip in a use position.
FIG. 4B is a longitudinal cross-sectional view of the distal portion of the device of FIG. 4A, taken along the line A-A of FIG. 4A.

As used herein, the terms "proximal" and "distal" are to be taken as relative to a user (e.g., a surgeon or an interventional cardiologist) using the disclosed devices. "Proximal" is to be understood as relatively close to the user and "distal" is to be understood as relatively farther away from the user. The invention will be described in connection with the repair of a mitral valve leaflet, but it may be useful in the repair of other types of cardiac valves or in the gathering and clamping of other types of loose body tissue.

Referring to FIG. 1, an exemplary mitral valve 1 includes a posterior leaflet 2 and an anterior leaflet 3. The leaflets 2 and 3 extend from an annulus 4 to a coaption line 5 where the leaflets meet. The posterior leaflet 2 has an upper portion 6 that is generally perpendicular to the direction of blood flow through the valve 1 and extends between the annulus and the coaption line 5. Additionally, the posterior leaflet 2 has a lower portion 7 that is generally parallel to the direction of blood flow through the valve 1 and extends below the coaption line 5. The posterior leaflet 2 also has a lower surface 9a and an upper surface 9b. The posterior leaflet 2 has three scalloped portions P1, P2, and P3, any of which may include a portion that is billowed, loose, or floppy, and which therefore may be the cause of a prolapse condition of the valve. The inventive devices, systems, and methods described herein may be adapted to repair such a billowed, loose, or floppy portion of the posterior leaflet 2 or the anterior leaflet 3.

Referring to FIG. 2A, an exemplary device 10 for transcatheter gathering of heart valve leaflet tissue includes an elongated catheter assembly 12 adapted to be inserted through the apex of a human heart so that a distal portion 14 of the catheter assembly may reach the patient's mitral valve 1 for repair thereof. The catheter assembly 12 includes a containment tube 20 disposed within an outer tube 16. In a particular embodiment, the outer tube 16 may be made of one or more echogenic materials, so that the outer tube may be more easily visualized inside a patient using three-dimensional echocardiography.

Figure 5A:
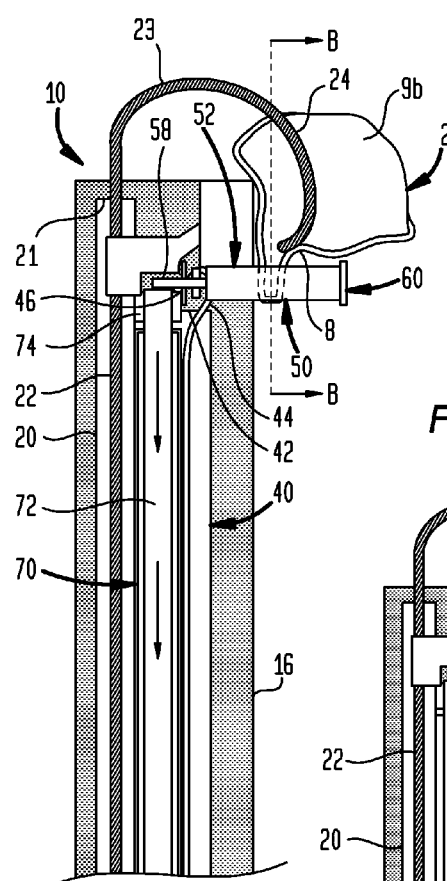
FIG. 5A is a longitudinal cross-sectional view of the distal portion of the device of FIG. 2A, engaged with the posterior leaflet of the mitral valve of FIG. 1.

The catheter assembly 12 further includes a capture tool in the form of a grasping wire 22 that is longitudinally slidable within the containment tube 20 between a retracted position substantially entirely within the lumen of the containment tube (FIG. 2A), and a deployed position in which a distal portion 23 of the grasping wire protrudes from the distal tip 21 of the containment tube (FIG. 5A). The grasping wire 22 may have a linear configuration when fully retracted within the containment tube 20 and the distal portion 23 thereof may assume the shape of a hook 24 when deployed from the containment tube. In that regard, the grasping wire 22 may be formed from a memory metal or a strong, resilient metal or polymer that will cause the hook 24 to form automatically when deployed.

The catheter assembly 12 further includes a tissue securing component in the form of a clip 50 that is adapted to secure tissue of a heart valve leaflet that is captured therein, as will be described below. As can be seen in FIG. 2C, the clip includes two rollers 52a and 52b (collectively, rollers 52). One or both of the rollers 52 may have a smooth outer surface 54, and one or both of the rollers may have a roughened or knurled surface, or a surface with protruding features (e.g., small spikes) that are configured to increase friction or gripping strength between the rollers and tissue of a heart valve leaflet that may be inserted between the rollers.

Each of the rollers 52 may be mounted between coupling plates 60a and 60b (collectively, coupling plates 60) that may be adapted to couple the rollers to one another with sufficient distance between the outer surfaces 54 thereof to permit heart valve leaflet tissue to extend therebetween. Although the embodiment shown in the figures has two coupling plates 60, in other embodiments, the rollers 52 may be coupled to a single coupling plate 60a, such that tissue may be inserted between adjacent ends 55 of the rollers as well as along the outer surfaces 54 of the rollers.

As shown in FIGS. 2C and 2D, each of the rollers 52 may be coupled to the coupling plates 60a and 60b by pins 56 extending through lumens of the rollers and through openings 62 in the coupling plates. Alternatively, separate pins 56 may respectively extend outwardly from each end of the rollers 52, as opposed to the pins extending therethrough. The pins 56 may each be affixed to a corresponding one of the rollers 52 and may be coupled to the coupling plates 60a and 60b by lock washers 66 that are adapted to retain the pins between the coupling plates while permitting one or both of the rollers 52a and 52b to rotate relative to the coupling plates around corresponding longitudinal axes L1 and L2. Each of the pins 56 may extend through the first coupling plate 60a such that an end portion 58 thereof is exposed beyond the coupling plate. Although as shown in the figures, both of the pins 56 have exposed end portions 58, in other embodiments, the second roller 52b may be provided without an exposed end portion, such that only the first roller 52a has an exposed end portion. In one example, one or both of the pins 56 may be formed integrally with or permanently attached to its corresponding roller 52, such that the pin may be considered to be a portion of the roller.

If it is desired that both rollers 52 be free to rotate about their longitudinal axes L1, L2, the pins 56 may both be rotationally coupled to the coupling plates 60. If it is desired that only the first roller 52a be free to rotate about its axis L1, the pin 56 of the first roller may be rotationally coupled to the coupling plates 60, while the pin of the second roller 52b may be affixed to the coupling plates. In a particular example, the second roller 52b may be a support element affixed between the coupling plates 60 that need not be generally in the shape of a cylinder. For example, such a support element could be a beam having a rectangular or arcuate cross-section.

A first one of the rollers 52a may rotate around its longitudinal axis L1 in only one rotational direction R1, for example. In the example shown in the figures, the unidirectional rotation of the first roller 52a may be enabled by interaction between an end 67 of a spring lock member 68 affixed at its base 69 to a first coupling plate 60a and teeth of a ratcheting cam 64. The ratcheting cam 64 may be affixed to the first roller 52a and may be adapted to rotate therewith relative to the spring lock member 68. The spring lock member 68 may be located to one side of a centerline C of the first coupling plate 60a and oriented substantially parallel to the centerline. As shown in FIG. 2C, the spring lock member 68 may be located above the centerline to enable rotation of the first roller 52a in a counterclockwise rotational direction R1 and to disable clockwise rotation thereof. Alternatively, the spring lock member 68 may be located below the centerline to enable clockwise rotation of the first roller 52a and to disable counterclockwise rotation thereof.

At its distal end 17, the outer tube 16 has an open side 15 that may provide clearance for the clip 50 to pivot away from the closed side 11 of the outer tube, so that the clip may be positioned to receive heart valve leaflet between the rollers 52 thereof, as will be described below.

The clip 50 may be removably coupled to an actuation shaft 40 that is slidably mounted within the outer tube 16 so that it may move relative to the outer tube along the longitudinal axis L3 of the outer tube. In its initial position (FIG. 2A), the clip 50 may be supported on a distal end 42 of the actuation shaft 40 so that the clip may be moved distally when the actuation shaft is moved distally. The clip 50 may be removably coupled to the actuation shaft 40 by a release wire 44, which may be a metal wire or a suture, for example. A distal end 46 of the release wire 44 may be removably attached to the clip 50 at or adjacent the first coupling plate 60a. A proximal end of the release wire 44 (not shown) may extend through the outer tube 16 to a location where it can be grasped by a user. In its initial position, the clip 50 may be oriented such that the longitudinal axes L1, L2 of the rollers 52 are substantially parallel to a longitudinal axis L3 of the outer tube 16.

The catheter assembly 12 further includes a contact plate 30 affixed to the outer tube 16. The contact plate 30 may have a guide surface 32 and an adjacent support surface 34. The guide surface 32 may be disposed at an oblique angle relative to the longitudinal axis L3 of the outer tube 16. The guide surface 32 may be adapted to guide motion of the clip 50. The support surface 34 may be disposed substantially perpendicular to the longitudinal axis L3 and may be adapted to support the exposed end portion 58 of the pin 56 extending through the first roller 52a, as will be described below.

The catheter assembly 12 may further include a drive assembly 70 that is slidably mounted within the outer tube 16 so that it may move relative to the outer tube along the longitudinal axis L3 of the outer tube. The drive assembly 70 may be adapted to rotate the first roller 52a relative to the outer tube about the longitudinal axis L1 of the first roller. The drive assembly 70 may include a support shaft 71 and a drive belt 72. The support shaft 71 may optionally have a lumen extending therethrough that is configured to receive the drive belt 72 therein. The drive assembly 70 may also include a drive roller 74 that is coupled to the support shaft 71 but is free to rotate relative to the support shaft about its longitudinal axis L4. The longitudinal axis L4 may be substantially perpendicular to the longitudinal axis L3 of the outer tube L3.

In a particular embodiment (not shown) the drive assembly 70 may be movable relative to the outer tube in a direction that is not substantially parallel to the longitudinal axis L3 of the outer tube 16. For example, the drive assembly 70 may be movable between an initial position and an engaged position (in which the drive assembly is engaged with the first roller 52a) in a direction that is substantially perpendicular to the longitudinal axis L3 of the outer tube 16.

The drive belt 72 may be assembled around the drive roller 74 and a support roller 75 (not visible in FIG. 2A, but shown in FIG. 4B) located distally of the drive roller. The support roller 75 may be either directly or indirectly coupled to the support shaft 71, and the drive roller may be free to rotate relative to the support shaft about its longitudinal axis. The support roller 75 may be located within the outer tube 16, and the rotation of the support roller may be actuated by a handle (not shown) at a proximal end of the catheter assembly 12, or the support roller may be located within such an actuation handle. The drive belt 72 may extend through a lumen of the support shaft 71, or it may extend along an outer surface of the support shaft. Examples of actuation handles for the devices described herein may be found in International Patent Publication No. WO 2012/106398, which is hereby incorporated by reference herein.

It is preferred that the drive assembly 70 include or be coupled to a torque limiter that is adapted to prevent a user from exceeding a predetermined torque that may damage tissue of the leaflet 2. Such a torque limiter may include a sensor that can determine the torque experienced by the rollers 52 and a mechanism for stopping the ability of the user to continue to actuate a control handle to actuate the drive assembly 70 if the predetermined maximum torque is reached.

To use the device 10 for transcatheter gathering of heart valve leaflet tissue, the support shaft 71 and the actuation shaft 40 may be initially disposed in their proximal positions shown in FIG. 2A, and the clip 50 may be initially disposed in its initial position shown in FIG. 2A, such that the longitudinal axes L1 and L2 of the rollers 52 are oriented substantially parallel to the longitudinal axis L3 of the outer tube 16.

Next, the distal portion 14 of the catheter assembly 12 may be inserted into a patient through the apex of the heart, for example, into the left ventricle, so that the distal portion extends between the posterior leaflet 2 and the anterior leaflet 3 of the mitral valve 1. The distal edge 17 of the outer tube 16 may be disposed near the coaption line 5 of the mitral valve 1, with the open side 15 of the outer tube facing the posterior leaflet 2. In a particular embodiment, the distal edge 17 of the outer tube 16 may be guided to a position near the coaption line 5 using the assistance of three-dimensional echocardiography to visualize the outer tube or other components of the catheter assembly 12.

Then, referring to FIG. 3, the actuation shaft 40 may be moved distally from its proximal position to an intermediate position. As the actuation shaft 40 moves distally relative to the outer tube 16, the second coupling plate 60b of the clip 50 may contact the guide surface 32 of the contact plate 30. When the second coupling plate 60b contacts the oblique angle of the guide surface 32, the guide surface will exert a rotational force onto the clip 50, such that continued distal movement of the actuation shaft 40 will pivot the clip about the first coupling plate 60a relative to the outer tube. FIG. 3 shows the clip 50 in an intermediate position that is partially pivoted relative to the actuation shaft 40, such that the longitudinal axes L1 and L2 are disposed at an oblique angle relative to the longitudinal axis L3 of the outer tube 16, and such that the second coupling plate 60b moves gradually away from the closed side 11 of the outer tube.

Subsequently, the actuation shaft 40 may continue to be moved distally from its intermediate position to the distal position shown in FIG. 4A. As the actuation shaft 40 continues to move distally relative to the outer tube 16, the clip continues to pivot about the first coupling plate 60a until the clip 50 reaches its use position, such that the longitudinal axes L1 and L2 are disposed substantially perpendicular to the longitudinal axis L3 of the outer tube. The pivoting of the clip 50 is eventually stopped by contact between the support surface 34 of the contact plate 30 and the exposed end portion 58 of the pin 56 of the first roller 52a.

Next, the support shaft 71 of the drive assembly may be moved distally from its initial position to the distal position shown in FIG. 4A. The support shaft 71 may be moved distally until the drive belt 72 contacts the exposed end portion 58 of the pin 56 of the first roller 52a. As can be seen in FIG. 4B, when the support shaft 71 is in its distal position, the exposed end portion 58 of the pin 56 of the first roller 52a is located between the support surface 34 of the contact plate 30 and the drive belt 72. In this position, rotation of the support roller 75 in a rotational direction R2 will rotate the drive belt 72 and the drive roller 74, which in turn, will rotate the exposed end portion 58 of the pin 56 of the first roller 52a in a direction R3 opposite the direction R2.

Then, as can be seen in FIG. 5A, the outer tube 16 can be manipulated by the user such that the rollers 52 at least partially extend underneath a portion of the posterior leaflet 2 of the mitral valve 1 that may be loose or floppy and require tightening. The hook 24 may then be deployed to an extended position by moving the distal portion 23 of the grasping wire 22 distally out of the containment tube 20. No longer being constrained by the containment tube 20, the distal portion 23 of the grasping wire 22 may assume the curved shape of the hook 24. It is preferable that the hook 24 have a curvature when deployed that is sufficient to push a portion of the posterior leaflet 2 against the rollers 52, as shown in FIG. 5A.

Figure 5B:
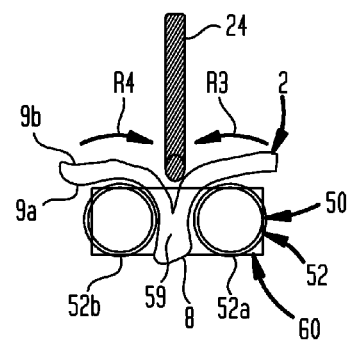
FIG. 5B is a side cross-sectional view of the clip of FIG. 5A, engaged with the posterior leaflet of the mitral valve of FIG. 1, taken along the line B-B of FIG. 5A.

Once the posterior leaflet 2 is pushed against the rollers 52, the user may actuate the drive assembly 70 to move the drive belt 72, thereby rotating the first roller 52a in the rotational direction R3 and rotating the second roller 52b in a rotational direction R4 opposite the direction R3 (or, only rotating the first roller in the direction R3 in an embodiment where the second roller is rotationally fixed). The rotation of the rollers 52 as the posterior leaflet 2 is pushed against the rollers will force a captured portion 8 of the leaflet into a gap 59 between the rollers, as can be seen in FIG. 5B.

The user may continue to actuate the drive assembly 70 to rotate one or both of the rollers 52 until the desired amount of tissue of the posterior leaflet 2 is advanced through the gap 59, or until a predetermined maximum torque experienced by the rollers is reached. Once the desired amount of tissue is secured by the clip 50, most or all of the portion of the posterior leaflet 2 that is billowed, loose, or floppy may be gathered and tightened. The clip 50 will remain clamped around the captured portion 8 of the posterior leaflet 2, thereby securing the tissue in the gathered configuration, because the interaction between the spring lock member 68 and the ratcheting cam 64 will prevent the first roller 52a from rotating in a direction opposite the rotational direction R3.

After the clip 50 has been adequately secured to the tissue of the posterior leaflet 2, the device 10 may be withdrawn from the patient. To withdraw the device 10, the hook 24 may first be withdrawn from engagement with the posterior leaflet 2 by moving the grasping wire 22 proximally. This action causes the hook 24 to straighten as the grasping wire 22 retracts into the containment tube 20.

Figure 6:
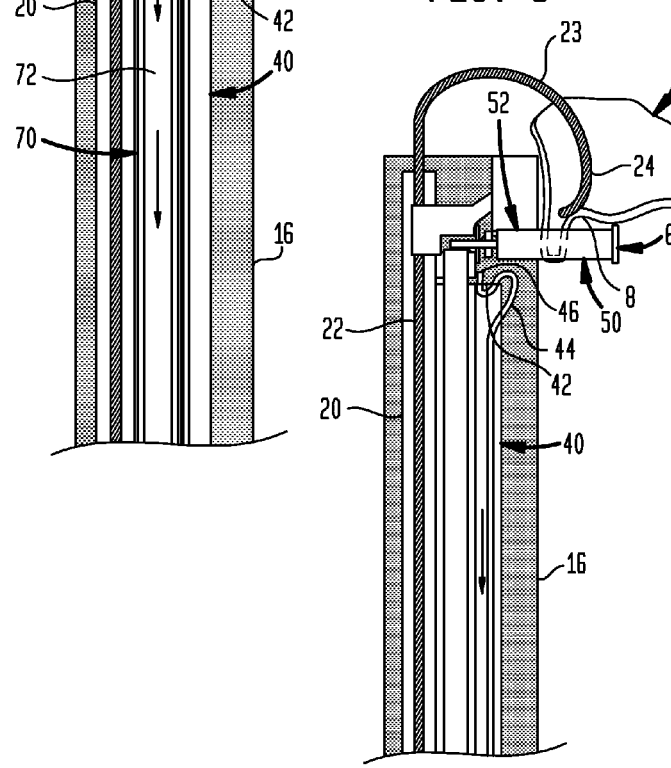
FIG. 6 is a longitudinal cross-sectional view of the distal portion of the device of FIG. 2A, shown with the release wire detached from the clip.

Then, the clip 50 can be detached from the device 10 by detaching the release wire 44 from the clip, as shown in FIG. 6. To detach the release wire 44, the user may pull proximally on the release wire until the release wire detaches from the clip 50. While the release wire 44 is being detached, the clip 50 is restrained from movement along the longitudinal axis L3 of the outer tube 16 because the exposed end portion 58 of the pin 56 of the first roller 52a is secured between the drive belt 72 and the support surface 34 of the contact plate 30. In embodiments where the release wire 44 is a suture, the suture may have a weakened portion near the location where the suture is attached to the clip 50, such that a small distal portion of the suture remains attached to the clip, but the rest of the suture becomes detached from the small distal portion when a sufficient proximal pulling force is reached.

Figure 7A:
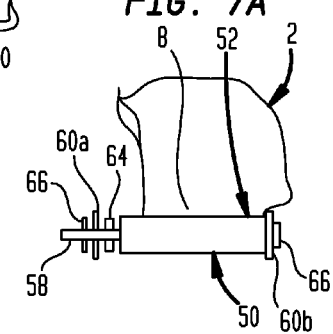
FIG. 7A is a side view of the clip of FIG. 2A, engaged with the posterior leaflet of the mitral valve of FIG. 1.
Figure 7B:
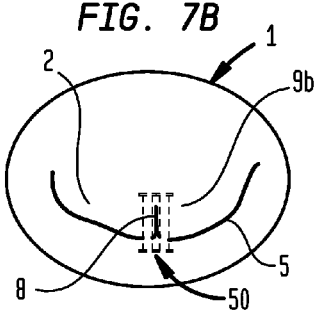
FIG. 7B is a top view of the clip of FIG. 2A, engaged with the posterior leaflet of the mitral valve of FIG. 1.

Subsequently, the user can move the support shaft 71 proximally, removing the support shaft from contact with the end portion 58 of the pin 56 of the first roller 52a, thereby releasing the clip 50 from being retained by the drive belt 72 and the support surface 34 of the contact plate 30 and completing deployment of the clip from the outer tube 16. Finally, the catheter assembly 12 may be withdrawn from the patient through the apex of the heart. After withdrawal of the device 10 from the patient, the clip 50 will remain clamped around the captured portion 8 of the posterior leaflet 2, as shown in FIGS. 7A and 7B. If desired, the procedure described above may be repeated to apply one or more additional clips 50 onto the same posterior leaflet 2.

An alternative embodiment of a device 110 for transcatheter gathering of heart valve leaflet tissue is shown in FIGS. 8A, 8B, 9A, and 9B. Similar to the device 10 described above, the device 110 includes an elongated catheter assembly 112 adapted to be inserted through the apex of a human heart so that a distal portion 114 of the catheter assembly may reach the patient's mitral valve 1 for repair thereof. The catheter assembly 112 includes a containment tube 120 disposed within an outer tube 116 along a longitudinal axis L5 of the outer tube. The outer tube 116 has an opening 118 that extends in a direction parallel to the longitudinal axis L5 and that extends partially around the circumference of the outer tube.

The catheter assembly 112 further includes a capture tool in the form of a grasping wire 122 that is longitudinally slidable within the containment tube 120 between a retracted position substantially entirely within the lumen of the containment tube, and a deployed position in which a distal portion 123 of the grasping wire protrudes from the distal tip 121 of the containment tube (FIG. 8A). The grasping wire 122 may have a linear configuration when fully retracted within the containment tube 120 and the distal portion 123 thereof may assume the shape of a hook 124 when deployed from the containment tube. When the grasping wire 122 is fully deployed from the containment tube 120 as shown in FIG. 9A, a contact portion 125 of the hook 124 extends to a location adjacent the opening 118. The contact portion 125 of the hook 124 may be marked with one or more radiopaque markers 126 so that the location of the contact portion can be more easily tracked by a user relative to the opening 118.

The catheter assembly 112 further includes a tissue securing component in the form of a clip 150 that is adapted to secure tissue of a heart valve leaflet that is captured therein, as will be described below. The clip 150 in the nature of an elongated member may be made of a memory metal and may be biased to curl into a substantially round configuration, such that the ends 151a and 151b (FIG. 8B) may overlap.

As can be seen in FIGS. 8A and 8B, the clip 150 in its initial condition extends around the peripheral edge 117 of the opening 118. The clip 150 may be assembled onto the outer tube 116 by extending around retention posts 152 that extend from an outer surface 111 of the outer tube in a direction substantially perpendicular to the outer surface. The clip 150 may include one or more radiopaque markers 156 thereon, so that the location of the radiopaque markers 126 on the contact portion 125 of the hook 124 can be more easily tracked by a user relative to the radiopaque markers on the clip. Furthermore, the radiopaque markers 156 on the clip 150 may allow a user to more easily track the location and/or orientation of the clip after it is deployed into tissue of the posterior leaflet 2.

The retention posts 152 may be retractable into the outer tube when actuated by a user operating a handle (not shown) that is adapted to retract the retention posts. The retention posts 152 can be retracted by pull wires (not shown) that are connected at their distal ends to bases of the respective retention posts, and that extend through one or more lumens along the catheter assembly 112 to a handle, where the pull wires can be grasped at their proximal ends and pulled in a proximal direction by a user, or actuated in a proximal direction by a mechanism of the handle that is controllable by a user.

As shown in FIG. 8A, the retention posts 152 are fully extended so that the clip 150 is retained in its initial condition extending around the peripheral edge 117 of the opening 118. When the retention posts 152 are retracted into the outer tube 116, the clip 150 is no longer retained around the peripheral edge 117, so the clip may contract according to its bias, thereby tightening into a smaller diameter (e.g., as shown in FIG. 11 clamped around a captured portion 8 of the posterior leaflet 2 when deployed.

Alternatively, the clip 150 may have a plurality of spaced-apart eyelets extending therethrough (not shown), and the clip may be assembled onto the outer tube 116 by being fastened to corresponding eyelets (not shown) in the retention posts 152. In this variation, rather than extending around outward-facing surfaces of the retention posts 152 (FIG. 8A), the clip 150 can extend along inward-facing surfaces of the retention posts. A single pull wire can extend through all of the eyelets in the clip 150 and in the retention posts 152, and both ends of the single pull wire can extend through a lumen extending along the catheter assembly 112 to a handle. To release the clip 150, one end of the single pull wire can be grasped and pulled in a proximal direction by a user, until the single pull wire is withdrawn from all of the eyelets in the clip 150 and in the retention posts 152, thereby releasing the clip so that it may contract according to its bias, thereby tightening into a smaller diameter.

The catheter assembly 12 further includes a roller 130 extending within the outer tube 116 substantially parallel to the longitudinal axis L5 of the outer tube. The roller 130 may have a lumen 132 (FIG. 9B) extending therethrough parallel to the longitudinal axis L5, and the containment tube 120 and the grasping wire 122 may extend through the lumen, or the lumen may serve as the containment tube for the grasping wire. Similar to the rollers 52 described above, the roller 130 may have a smooth outer surface 134, a roughened or knurled surface, or a surface with protruding features (e.g., small spikes) that are configured to increase friction or gripping strength between the roller and tissue of a heart valve leaflet that may be inserted into the outer tube 116 adjacent the roller.

The roller 130 may be coupled to a drive assembly (not shown) that is operable to rotate the roller about its longitudinal axis, such drive assembly being available to be actuated by a user by control of an actuation handle (not shown). In one example, such a drive assembly may include belts and rollers that similar to the drive assembly 70 described above that can rotate the roller 130 in response to a user moving a button or wheel of an actuation handle. It is preferred that such a drive assembly include or be coupled to a torque limiter that is adapted to prevent a user from exceeding a predetermined torque that may damage tissue of the leaflet 2.

A pocket 113 (FIG. 10B) may be defined inside the outer tube 116 between an inner surface 119 of the outer tube and the outer surface 134 of the roller. The roller 130 may be centered within the outer tube 116, such that the lumen 132 of the roller extends along the longitudinal axis L5 of the outer tube, as shown in FIG. 9B, for example, so that there may be a pocket 113 on both sides of the roller. In other embodiments, the roller 130 may be offset relative to the longitudinal axis L5 of the outer tube 116, such that there may be a single pocket 113 on a first side of the roller, and such that a second side of the roller opposite the first side is disposed adjacent the inner surface 119 of the outer tube with a minimal clearance.

To use the device 110 for transcatheter gathering of heart valve leaflet tissue, the clip 150 may be initially disposed in its initial position shown in FIG. 8A extending about the opening 118 and around the retention posts 152, the retention posts being disposed in their extended positions.

Next, the distal portion 114 of the catheter assembly 112 may be inserted into a patient through the apex of the heart, for example, into the left ventricle, so that the distal portion extends between the posterior leaflet 2 and the anterior leaflet 3 of the mitral valve 1. The opening 118 of the outer tube 116 may be disposed near the coaption line 5 of the mitral valve 1, with the opening of the outer tube facing the posterior leaflet 2. The distal end 121 (FIG. 8A) of the containment tube 120 (FIG. 9B) may be disposed above the coaption line 5, such that the hook 124 may contact the upper surface 9b of the posterior leaflet 2 when the hook is moved to its extended position.

Then, referring to FIG. 9A, the hook 124 may then be deployed to an extended position by moving the distal portion 123 of the grasping wire 122 distally out of the containment tube 120. No longer being constrained by the containment tube 120, the distal portion 123 of the grasping wire 122 may assume the curved shape of the hook 124. It is preferable that the hook 124 have a curvature when deployed that is sufficient to push a portion of the posterior leaflet 2 into the opening 118, as shown in FIG. 9A.

Once the hook 124 is extended full so that the contact portion 125 thereof has pushed a portion of the posterior leaflet 2 into the opening 118 of the outer tube 116, the user may actuate a drive assembly (not shown) rotate the roller 130 in the rotational direction R5 (FIG. 10B). The rotation of the roller 130 as the posterior leaflet 2 is pushed against it will force a captured portion 8 of the leaflet into the opening 118 and into the pocket 113 between the roller and the inner surface 119 of the outer tube 116, as can be seen in FIG. 10B.

The user may continue to actuate the drive assembly to rotate the roller 130 until the desired amount of tissue of the posterior leaflet 2 is advanced into the pocket 113, or until a predetermined maximum torque experienced by the rollers is reached. Once the desired amount of tissue is disposed in the pocket 113, the clip 150 may be deployed onto the captured portion 8 of the posterior leaflet 2 by retracting the retention posts 152 into the outer tube 116. Once the retention posts 152 are removed from contact with the clip 150, the clip will contract around the captured portion 8 of the posterior leaflet 2 as can be seen in FIGS. 10A and 11. Once the captured portion 8 has been secured by the clip 150, most or all of the portion of the posterior leaflet 2 that is billowed, loose, or floppy may be gathered and tightened.

After the clip 50 has been adequately secured in the tissue of the posterior leaflet 2, the device 110 may be withdrawn from the patient. To withdraw the device 110, the hook 124 may first be withdrawn from engagement with the posterior leaflet 2 by moving the grasping wire 122 proximally. This action causes the hook 124 to straighten as the grasping wire 122 retracts into the containment tube 120.

Then, the captured portion 8 of the posterior leaflet 2 may be removed from the pocket 113 of the outer tube 116 by rotating the roller 130 in a direction opposite the direction R5 that was used to gather the leaflet tissue in the pocket. Rotating the roller 130 in this opposite direction will push the captured portion 8 out of the pocket 113 and out of the opening 118 of the outer tube 116.

After the captured portion 8 of the posterior leaflet 2 is removed from the outer tube 116, the catheter assembly 112 may be withdrawn from the patient through the apex of the heart. After withdrawal of the device 110 from the patient, the clip 150 will remain clamped around the captured portion 8 of the posterior leaflet 2, as shown in FIG. 11. If desired, the procedure described above may be repeated to apply one or more additional clips 150 onto the same posterior leaflet 2.

In another alternate embodiment, as shown in FIG. 12, a device 110*a* may include two rollers 130*a* and 130*b* extending within the elongated tube 116*a*, each roller having a rotational axis substantially parallel to the longitudinal direction of the outer tube 116*a*, such that a pocket 113*a* is defined between adjacent outer surfaces 134 of the rollers. In such an embodiment, when leaflet tissue is drawn into the opening 118, the first roller 130*a* may be rotated in a first rotational direction R6, and friction between captured tissue and the first and second rollers will cause the second roller 130*b* to rotate in a second rotational direction R7 opposite the first rotational direction. Alternatively, both of the rollers 130*a*, 130*b* may be rotated by a user in respective opposite directions R6, R7. The device 110*a* may include a capture tool in the form of a grasping wire 122*a* that is longitudinally slidable within a containment tube 120*a*, similar to the grasping wire 122 and the containment tube 120 described above, except that the containment tube 120*a* may be located adjacent an inner surface 119 of the outer tube 116*a* at a periphery of the pocket 113*a*.

Yet another alternative embodiment of a device 110*b* for transcatheter gathering of heart valve leaflet tissue is shown in FIGS. 13A and 13B. The device 110*b* is similar to the device 110 described above, but the device 110*b* includes an alternate outer tube arrangement. As shown in FIGS. 13A and 13B, the device 110*b* has two openings 118*a* and 118*b* at opposite sides of the outer tube 116*b*.

In use for gathering and securing of leaflet tissue, the device 110*b* functions similarly as the device 110 described above, except that rather than gathering tissue in a pocket inside the outer tube, the roller 130 of the device 110*b* rotates in a direction R8 to guide the captured portion 8 of the posterior leaflet 2 into the outer tube 116*b* via the first opening 118*a* and out of the outer tube via the second opening 118*b*. Once the desired amount of leaflet tissue has been passed through the outer tube 116*b*, the retention posts 152 can be retracted into the outer tube, and the clip 150 can released to clamp around the captured portion 8 of the posterior leaflet 2. Finally, the roller 130 can be rotated in a direction that is the reverse of the direction R8 to withdraw the captured portion 8 from the outer tube 116*b*. After the clamped tissue has been withdrawn from the device 110*b*, the device may be withdrawn from the patent.

Still another alternative embodiment of a device 110*c* for transcatheter gathering of heart valve leaflet tissue is shown in FIGS. 14A and 14B. The device 110*c* is similar to the device 110*b* described above, but the device 110*c* includes an alternate outer roller arrangement. As shown in FIGS. 14A and 14B, the device 110*c* has a roller 130*c* having an oblong cross-section. Such a roller 130*c* may provide a better gripping force between the surface 134*c* of the roller and a captured portion 8 of the posterior leaflet 2. In use for gathering and securing of leaflet tissue, the device 110*c* functions similarly as the device 110*b* described above.

Another alternative embodiment of a device 110*d* for transcatheter gathering of heart valve leaflet tissue is shown in FIG. 15. The device 110*d* is similar to the device 110*b* described above, but the device 110*d* includes an alternate clip arrangement. As shown in FIG. 15, the device 110*d* has a first clip 150*a* extending around the first opening 118*a* of the outer tube 116*d* and a second clip 150*b* extending around the second opening 118*b* of the outer tube.

The first clip 150*a* and the second clip 150*b* may have a different pattern of radiopaque markers so that the orientation of the outer tube 116*d* can be more easily determined by the user. For example, the first clip 150*a* can have one radiopaque marker 156*a* thereon, and the second clip 150*b* can have two radiopaque markers 156*b* thereon. Such a device 110*c* having two clips 150*a*, 150*b* can permit a user more flexibility after insertion of the device into a patient. For example, either of the clips 150*a* or 150*b* may be used to capture tissue of the posterior leaflet 2, depending on which clip is facing the posterior leaflet. In use for gathering and securing of leaflet tissue, the device 110*d* functions similarly as the device 110*b* described above.

In the devices shown in the figures, particular structures are shown that are adapted to gather, secure, and repair heart valve leaflet tissue. The invention also contemplates the use of any alternative structures for such purposes, including structures having different lengths, shapes, and configurations. For example, although the capture tool is shown in the form of a grasping wire 22 or 122, the capture tool may take other forms, including for example, a pincer-like structure such as a clamp. Furthermore, although the grasping wires 22 and 122 are shown as having a hook 24 and 124, respectively, the distal portion of the grasping wire may have any shape or configuration that may be adapted to grasp a target portion of valve leaflet tissue and help to capture such tissue inside or adjacent the outer tube such that a clip may be applied to the captured tissue.

Although the devices described herein are shown as being adapted to apply a single clip 50 or 150 onto a posterior leaflet 2, the invention contemplates devices that are adapted to apply a plurality of clips to the leaflet tissue during a single insertion of the device into a patient. For example, the retention posts 152 may be long enough to accommodate a plurality of clips 150 thereon. In such an embodiment, while leaflet tissue is captured within the outer tube 116, the retention posts 152 may be retracted to a first position to apply a first clip 150 to the tissue at a first target location, and the retention posts may then be further retracted to a second position to apply a second clip 150 to the tissue at a second target location spaced from the first location.

Although the various gathering devices have been described herein in connection with tightening the posterior leaflet of a mitral valve, all of these devices may be used on other heart valve leaflets, such as the anterior leaflet of the mitral valve, or on any other tissue of the body for which a reduction in the length of the tissue would be beneficial.

Although the invention herein has been described with reference to particular embodiments in which the catheter assembly is inserted into the patient through the apex of the heart (i.e., transapical insertion), it is to be understood that the invention contemplates embodiments in which the catheter assembly extends through a portion of the vasculature of the patient to reach the heart, for example, through a transfemoral or subclavian artery, or using a transseptal procedure. Any other percutaneous technique for accessing the interior of the heart may also be used. In such embodiments, some of the device components may have to be oriented in a different direction to that described herein. For example, the invention contemplates embodiments in which the distal portion of the catheter assembly approaches the mitral valve from the upstream side as well as from the downstream side of the valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A device for transcatheter gathering of tissue of a heart valve leaflet, comprising:
    an elongated tube extending in a longitudinal direction and having an open distal end, the elongated tube having an inner surface and a lumen extending therethrough; and
    a tissue securing component disposed at the distal end of the elongated tube, the tissue securing component comprising a clip including a roller and a support element, the roller being rotatable relative to the support element,
    wherein the tissue securing component is adapted to be applied to the captured tissue to hold the captured tissue in a gathered configuration, and
    wherein the roller is configured to rotate about a rotational axis of the roller only in a first rotational direction and not in a second rotational direction opposite the first rotational direction.

2. The device of claim 1, wherein the tissue securing component is releasable from the elongated tube so as to remain on the tissue as the elongated tube is removed from the tissue.

3. The device of claim 1, wherein the roller is a first roller and the support element is a second roller, the second roller being rotatable relative to the first roller.

4. The device of claim 1, wherein the roller is a first roller and the support element is a second roller, the second roller being fixed relative to a rotational axis of the first roller.

5. The device of claim 1, wherein the support element is fixed relative to a rotational axis of the roller.

6. The device of claim 1, wherein the tissue securing component includes two coupling plates extending between the roller and the support element.

7. The device of claim 1, wherein the roller has an outer surface that is roughened, knurled, or having features that protrude from the outer surface.

8. The device of claim 1, further comprising a drive assembly adapted to rotate the roller relative to the support element.

9. The device of claim 8, wherein the drive assembly is movable in the elongated tube in the longitudinal direction, the drive assembly being movable between a proximal position in which a distal end of the drive assembly is spaced apart from the roller and a distal position in which the distal end of the drive assembly contacts a portion of the roller.

10. The device of claim 9, wherein the drive assembly includes a belt extending around two rollers.

11. The device of claim 1, further comprising an actuation shaft movable in the elongated tube in the longitudinal direction, the actuation shaft adapted to move the tissue securing component therewith relative to the elongated tube.

12. The device of claim 11, further comprising a contact plate having a guide surface disposed at an oblique angle relative to the longitudinal direction, the guide surface being adapted to guide motion of the tissue securing component such that the roller pivots relative to the actuation shaft about an axis perpendicular to a rotational axis of the roller when the actuation shaft is moved distally.

13. The device of claim 12, further comprising a capture tool movable in the elongated tube between a retracted position and an extended position, the capture tool being operable to capture the tissue of the heart valve leaflet and to draw the captured tissue into the tissue securing component.

14. The device of claim 11, further comprising a release wire removably coupled to the tissue securing component and extending through the elongated tube to a proximal end of the device.

15. The device of claim 2, further comprising a capture tool movable in the elongated tube between a retracted position and an extended position, the capture tool being operable to capture the tissue of the heart valve leaflet and to draw the captured tissue into the tissue securing component.

16. The device of claim 15, wherein a distal end of the capture tool has a hook shape.

17. The device of claim 16, wherein the capture tool includes a grasping wire slidably disposed in a containment tube, and a distal portion of the grasping wire is adapted to change from a linear shape to the hook shape when the distal portion of the grasping wire is extended out from the containment tube.

18. The device of claim 17, wherein the grasping wire is partially or entirely made from a shape-memory material.

19. The device of claim 1, further comprising a capture tool movable in the elongated tube between a retracted position and an extended position, the capture tool being operable to capture the tissue of the heart valve leaflet and to draw the captured tissue into the tissue securing component.

20. The device of claim 1, wherein the tissue securing component includes a ratchet permitting rotation of the roller about the rotational axis of the roller only in the first rotational direction, the ratchet preventing rotation of the roller in the second rotational direction.

* * * * *